(12) United States Patent
Perazzolo Gallo et al.

(10) Patent No.: US 9,168,367 B2
(45) Date of Patent: Oct. 27, 2015

(54) HAND HELD ADJUSTABLE DEVICE

(75) Inventors: Giacomo Perazzolo Gallo, Cerea (IT); Ruggero Cadossi, Carpi (IT); Donata Marazzi, Carpi (IT); Claudio Bertacchini, Carpi (IT)

(73) Assignee: IGEA S.p.A., Carpi (IT)

( * ) Notice: Subject to any disclaimer, the term of this patent is extended or adjusted under 35 U.S.C. 154(b) by 0 days.

(21) Appl. No.: 14/110,135

(22) PCT Filed: Apr. 5, 2012

(86) PCT No.: PCT/IB2012/051712
§ 371 (c)(1),
(2), (4) Date: Dec. 23, 2013

(87) PCT Pub. No.: WO2012/137176
PCT Pub. Date: Oct. 11, 2012

(65) Prior Publication Data
US 2014/0148884 A1    May 29, 2014

(30) Foreign Application Priority Data
Apr. 5, 2011 (IT) .............. TO2011-A0309

(51) Int. Cl.
*A61N 1/00* (2006.01)
*A61N 1/04* (2006.01)
*A61N 1/32* (2006.01)
*A61B 18/14* (2006.01)

(52) U.S. Cl.
CPC .............. *A61N 1/0412* (2013.01); *A61N 1/327* (2013.01); *A61B 2018/143* (2013.01); *A61B 2018/1475* (2013.01)

(58) Field of Classification Search
CPC . A61N 1/0412; A61N 1/0424; A61N 1/0476; A61N 1/0502; A61N 1/327; A61B 2018/1475; A61B 2018/143
USPC .................. 607/115, 116, 145, 147, 149–151
See application file for complete search history.

(56) References Cited

U.S. PATENT DOCUMENTS

| 5,873,877 A | * | 2/1999 | McGaffigan et al. ........... 606/41 |
| 2005/0267552 A1 | * | 12/2005 | Conquergood et al. ......... 607/96 |
| 2008/0200864 A1 | | 8/2008 | Holzbaur et al. |
| 2008/0281389 A1 | * | 11/2008 | Knopp et al. ................. 607/115 |
| 2010/0298825 A1 | | 11/2010 | Slizynski et al. |

OTHER PUBLICATIONS

PCT International Search Report for PCT Counterpart Application No. PCT/IB2012/051712, 3 pgs., (Jul. 26, 2012).
PCT Written Opinion of the International Searching Authority for PCT Counterpart Application No. PCT/IB2012/051712, 5 pgs., (Jul. 26, 2012).

* cited by examiner

*Primary Examiner* — Michael Kahelin
*Assistant Examiner* — Mallika D Fairchild
(74) *Attorney, Agent, or Firm* — Blakely, Sokoloff, Taylor & Zafman LLP

(57) ABSTRACT

Hand held adjustable device comprising: a grip provided with an end portion; a plurality of needles which extend axially from the end portion and are made of electrically conductive material, and a device for adjusting the insertion depth of the needles in a tissue in which a cup-shaped body borne by said end portion of the grip is provided with an end wall having holes for the passage of said needles. A system for adjustment of the relative position between the cup-shaped body and the end portion provides an axial sliding of the cup-shaped body with respect to the end portion adjust the length of the portion of the needles protruding from said end wall and therefore the insertion depth in the tissue.

7 Claims, 5 Drawing Sheets

FIG. 4
FIG. 5
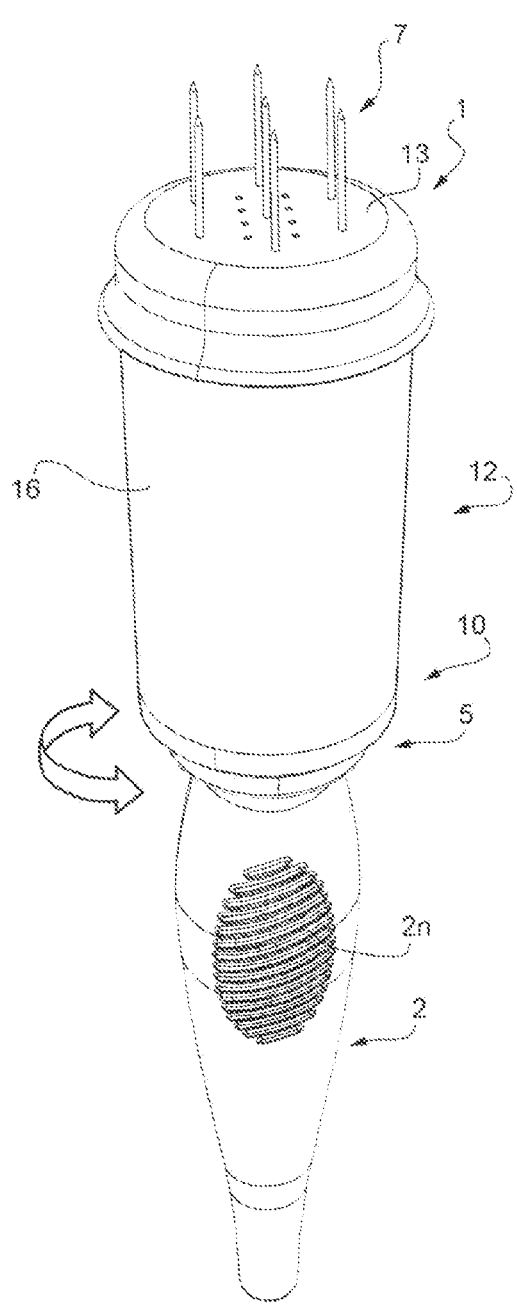
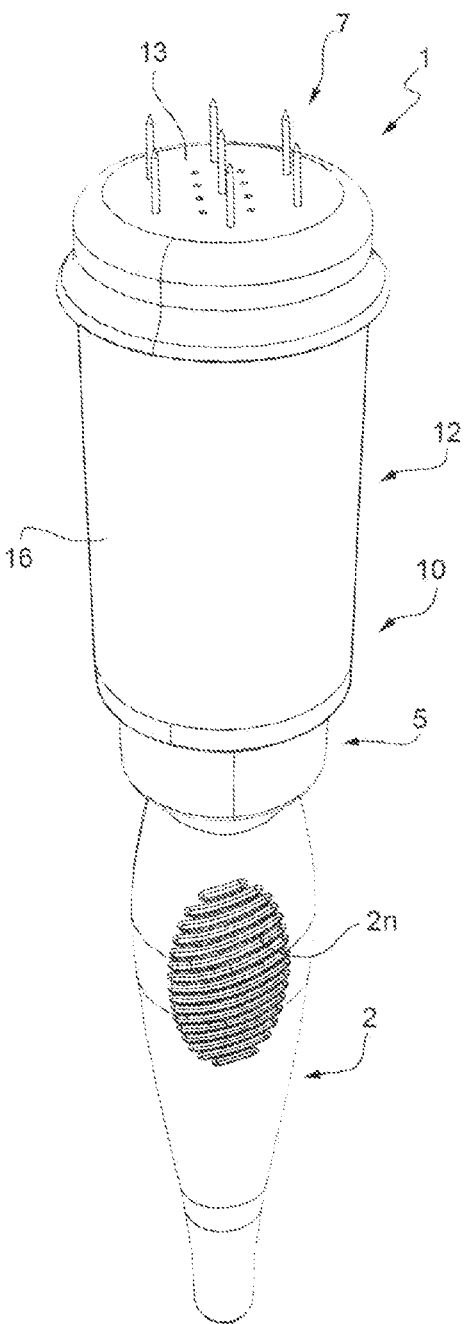

HAND HELD ADJUSTABLE DEVICE

CROSS-REFERENCE TO RELATED APPLICATIONS

This patent application is a U.S. National Phase Application under 35 U.S.C. §371 of International Application No. PCT/IB2012/051712, filed Apr. 5, 2012, entitled HAND HELD ADJUSTABLE DEVICE, which claims priority to Italian Patent Application No. TO2011A000309, filed Apr. 5, 2011.

TECHNICAL FIELD

The present invention concerns a hand held adjustable device which can be used, for example, for electroporation treatment.

BACKGROUND ART

As is known, electroporation treatments entail the application of electrical impulses to an organic tissue via the use of electrodes applied to the tissue; the electric field generated in the tissue produces the formation of pores in the cellular plasmatic membrane causing a variation in its permeability which facilitates the flow of organic/inorganic substances (for example DNA or drugs) from the outside to the inside of the cell. Said electroporation treatments can be controlled on the basis of the parameters (voltage, waveform, duty-cycle, application time, number of impulses applied, etc.) of the electrical impulses. In some applications the electrodes are inserted in the tissue to make the electroporation process more effective; for example the electrodes can comprise a plurality of needles which extend from a grip made of insulating material. The needles are electrically connected to a source of electrical impulses and are inserted in the part of the body of a patient where the electroporation treatment is required.

SUMMARY

The object of the present invention is to produce a hand held device provided with a plurality of needles which allows, in a simple effective manner, adjustment of the needle insertion depth in the portion of tissue.

The preceding object is achieved by the present invention as it relates to a hand held adjustable device comprising: a grip provided with an end portion; a plurality of needles which extend axially from the end portion and are made of electrically conductive material, characterised in that means for adjusting the insertion depth of the needles in a tissue are provided comprising a cup-shaped body borne by said end portion of the grip and provided with an end wall provided having holes for the passage of said needles; a system is provided for adjustment of the relative position between said cup-shaped body and the end portion suitable for providing an axial sliding of the cup-shaped body with respect to the end portion and adjusting the length of the portion of the needles which protrudes from said end wall.

BRIEF DESCRIPTION OF THE DRAWINGS

The invention will now be illustrated with reference to the accompanying drawings which represent a preferred non-limiting example of embodiment in which:

FIG. 4 illustrates the hand held device in a first operating position;

FIG. 5 illustrates the hand held device in a second operating position; and

DETAILED DESCRIPTION

Figure 1:
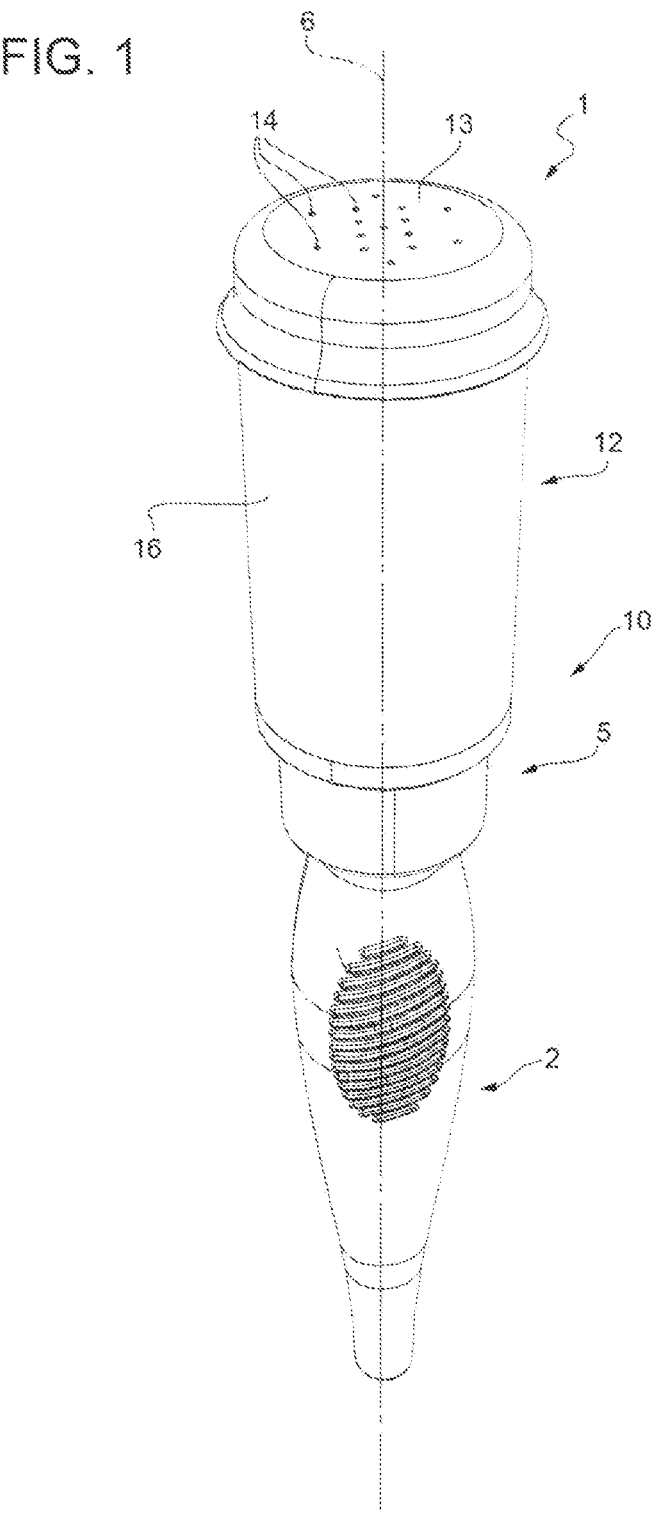
FIG. 1 illustrates, in a perspective view, a hand held device produced according to the present invention.
Figure 2:
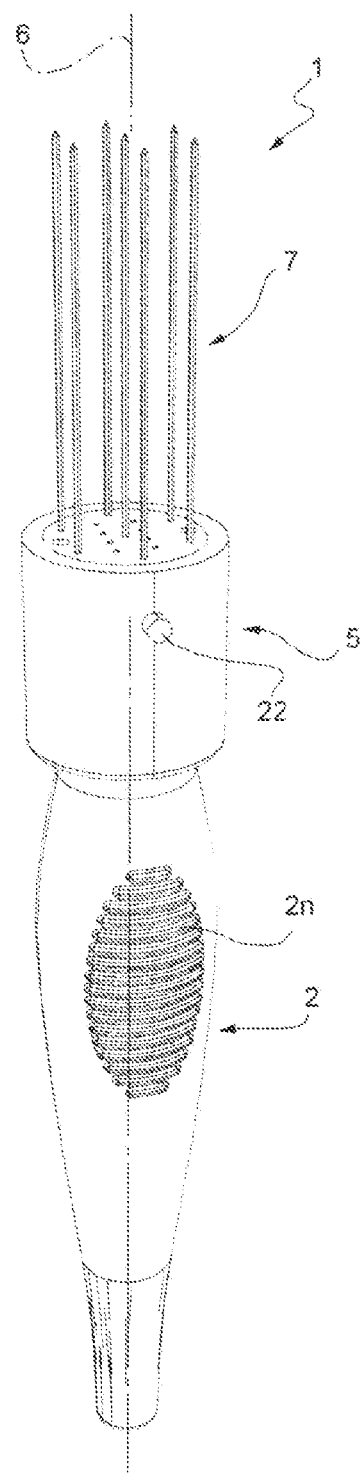
FIG. 2 illustrates the hand held device of FIG. 1 with a part removed to illustrate the internal parts.

In FIGS. 1, 2, 4 and 5, the reference number 1 indicates, as a whole, a hand held adjustable device comprising an elongated grip 2 provided with a cylindrical end portion 5 (see FIG. 2) coaxial with an axis 6, and a plurality of rectilinear needles 7 (FIGS. 2, 4 and 5) which extend along the axis 6 from the cylindrical end portion 5 and are made of an electrically conductive material like steel. In the example illustrated all the needles 7 have the same length, for example 30 or 40 millimeters. The needles can have a different section, for example circular or hexagonal. A portion of the needles 7 could be covered by an insulating sheath (not illustrated). The grip 2 is made of insulating material (for example plastic) and is provided with a plurality of non-slip ribs 2n.

According to the present invention, a device 10 is provided for adjusting the insertion depth of the needles 7 comprising a cup-shaped body 12 borne by the cylindrical end portion 5 and provided with a flat end wall 13 transversal to the axis 6 and having holes 14 (FIG. 1) for the passage of the needles 7. The device 10 comprises a system for adjusting the relative position between the cup-shaped body 12 and the end portion 5 suitable for providing an axial sliding of the cup-shaped body 12 with respect to the end portion 5 and adjusting the length of the portion of the needles 7 which protrudes from the flat end wall 13.

The cup-shaped body 12 comprises a cylindrical tubular side wall 16 positioned coaxial to the axis 6 and the end wall 13 which has a flat circular form and is transversal to the cylindrical tubular side wall 16 and to the axis 6. The cup-shaped body 12 is made of clear insulating plastic.

Figure 3:
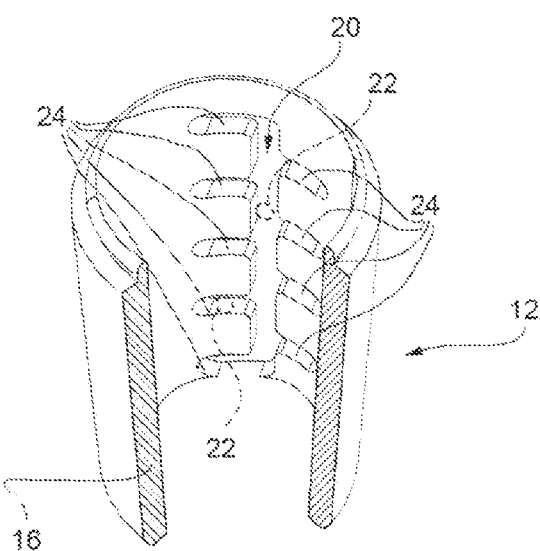
FIG. 3 illustrates in a perspective view and partially in section a portion of the hand held device of FIGS. 1 and 2.
Figure 6:
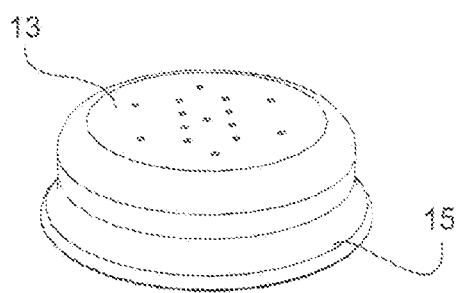
FIG. 6 illustrates, in an exploded perspective view, a detail of the hand held device illustrated in FIGS. 1, 4 and 5.
Figure 6:
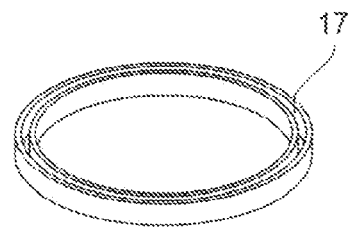

Advantageously, the end wall 13 is defined by a plug element which can rotate with respect to the cylindrical side wall 16 to allow rotation of the wall 16 of the cup-shaped body 12 with respect to the needles 7 which are fixed. More specifically, the plug element—also having a cup-shaped form—comprises the flat circular wall 13 which is integral with a cylindrical tubular edge 15; the latter is snap-fitted, by the interposition of a ring-shaped gasket 17 which allows an angular movement, on an end edge 16f (FIG. 3) of the tubular wall 16.

The position adjustment device 10 comprises a rectilinear groove 20 (FIG. 3) which extends in an axial direction along the side wall 16, and a cylindrical stop element 22 (FIG. 2) which extends in a radial direction from a side wall of the end portion 5 engaging the groove 20 (the diameter of the stop element 22 is substantially equal to the width of the groove 20). The groove 20 communicates with a plurality of short rectilinear transversal seats 24 perpendicular to the groove 20 and equi-spaced from one another along the groove 20. In this way the groove 20 and the seats 24 (which have the same length) have the shape of a double comb (FIG. 3) when seen from the side. When the stop element 22 is housed in a seat 24 (FIG. 3), an axially fixed position is achieved between the cup-shaped body 12 and the cylindrical portion 5 since the stop element 20 abuts against opposite portions of the seat 24 preventing sliding of the cup-shaped body 12. When the stop element 22 is housed in the groove 20, an axially adjustable position is obtained between the cup-shaped body 12 and the cylindrical portion 5 since the stop element 22 can slide in the groove 20. The passage from the axially fixed position to the axially adjustable position and vice versa is obtained by rotating (see arrow in FIG. 4) the cup-shaped body 12 with respect to the cylindrical portion 5.

By arranging the stop element 22 in different seats 24, a plurality of stable axial positions are obtained between the cup-shaped body 12 and the end portion 5.

In use, the hand held device allows treatment to be performed (for example electroporation treatment) in two ways:
i) The cup-shaped body 12 is made to rotate and slide axially so that the cylindrical stop element 22 is positioned in a selected seat 24—in this way the insertion depth of the needles 7 in the tissue is adjusted by adjusting the length of the portion of needles 7 which protrudes from the wall 13. The FIGS. 4 and 5 illustrate two different arrangements of the cup-shaped body corresponding to two different lengths of the portion of needles 7 protruding from the wall 13. The selection system is a simple roto-translation (see arrow in FIG. 4) of the cup-shaped body 12 until it reaches the seat 24. The movement allows step selection (for example of 5 mm).
ii) The cylindrical stop is positioned in the groove 20 so that the cup-shaped body 12 can slide with respect to the cylindrical portion 5—in this way, the operator can "push" the needles 7 to the required depth inside the tissue, while guiding them. This characteristic allows problems of misalignment of the needles 7 from the axis 6 to be considerably reduced.

What is claimed is:

1. A hand held adjustable device comprising:
a grip provided with an end portion;
a plurality of needles which extend axially from the end portion and are made of electrically conducting material,
wherein means for adjusting mechanically the maximum depth of introduction of the needles in a tissue are provided, comprising a cup-shaped body borne by said end portion of the grip and provided with an end wall provided with holes for the passage of said needles;
a system for mechanically adjusting the relative position between said cup-shaped body and the end portion adapted to provide a manual axial sliding of the cup-shaped body with respect to the end portion to allow for a number of stable axial positions between said cup-shaped body and said end portion and adjust the length of the portion of the needles that projects from said end wall in order to establish a number of different lengths,
wherein said system for adjusting the relative position comprises a groove which extends axially along a side wall of said cup-shaped body and a stop element that extends radially from said end portion of the grip and engages said groove, said groove further comprises a plurality of transversal seats spaced along the groove itself and for defining respective stable axial positions.

2. The hand held adjustable device according to claim 1, wherein said cup-shaped body is made of a transparent material.

3. The hand held adjustable device according to claim 1, wherein said cup-shaped body comprises a cylindrical tubular side wall and said end wall transversal to said cylindrical tubular side wall.

4. The hand held adjustable device according to claim 3, wherein said end wall is defined by a plug element that can rotate with respect to the cylindrical tubular side wall.

5. The hand held adjustable device according to claim 4, wherein said plug element comprises said circular flat end wall which is integral with a cylindrical tubular edge which can be snap-fitted with the possibility of moving angularly, by a gasket for interposition on an end edge of said tubular wall.

6. The hand held adjustable device according to claim 1, wherein said grip houses a plurality of electrical conductors for connecting said needles to a source of pulses comprising an electroporation apparatus.

7. A hand held adjustable device comprising:
a grip provided with an end portion;
a plurality of needles which extend axially from the end portion and are made of electrically conducting material,
wherein means for adjusting mechanically the maximum depth of introduction of the needles in a tissue are provided, comprising a cup-shaped body borne by said end portion of the grip and provided with an end wall provided with holes for the passage of said needles;
a system for mechanically adjusting the relative position between said cup-shaped body and the end portion adapted to provide a manual axial sliding of the cup-shaped body with respect to the end portion and an angular movement between said cup-shaped body and the end portion to select a number of stable axial positions between said cup-shaped body and said end portion and adjust the length of the portion of the needles that projects from said end wall in order to establish a number of different lengths,
wherein said system for adjusting the relative position comprises a groove which extends axially along a side wall of said cup-shaped body and a stop element that extends radially from said end portion of the grip and engages said groove, said groove further comprises a plurality of transversal seats spaced along the groove itself and for defining respective stable axial positions.

* * * * *